United States Patent
Zheng et al.

(10) Patent No.: US 8,124,944 B2
(45) Date of Patent: Feb. 28, 2012

(54) MICROARRAY READER BASED ON EVANESCENT WAVE DETECTION AND METHOD OF READING A MICROARRAY

(75) Inventors: Yuan Zheng, Shanghai (CN); Leon Xu, Shanghai (CN); Zhenhong Sun, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/522,188

(22) PCT Filed: Jan. 17, 2007

(86) PCT No.: PCT/CN2007/000020
§ 371 (c)(1),
(2), (4) Date: Jan. 5, 2010

(87) PCT Pub. No.: WO2008/092291
PCT Pub. Date: Aug. 7, 2008

(65) Prior Publication Data
US 2010/0148092 A1 Jun. 17, 2010

(51) Int. Cl.
*G01N 21/64* (2006.01)
(52) U.S. Cl. .................................. 250/459.1
(58) Field of Classification Search .............. 250/458.1, 250/459.1; 435/5, 6
See application file for complete search history.

(56) References Cited

U.S. PATENT DOCUMENTS

| | | | |
|---|---|---|---|
| 5,585,242 A | 12/1996 | Bouma et al. | |
| 5,776,672 A | 7/1998 | Hashimoto et al. | |
| 5,843,651 A | 12/1998 | Stimpson et al. | |
| 6,015,674 A | 1/2000 | Woudenberg et al. | |
| 6,207,381 B1 | 3/2001 | Larsson et al. | |
| 6,270,965 B1 | 8/2001 | Kleiber et al. | |
| 6,379,897 B1 | 4/2002 | Weidenhammer et al. | |
| 6,638,722 B2 | 10/2003 | Ji et al. | |
| 7,170,597 B1 * | 1/2007 | Hooper et al. | 356/317 |
| 2001/0020588 A1 | 9/2001 | Adourian et al. | |
| 2002/0102595 A1 | 8/2002 | Davis | |
| 2002/0164629 A1 | 11/2002 | Quake et al. | |
| 2002/0177144 A1 * | 11/2002 | Remacle et al. | 435/6 |

(Continued)

FOREIGN PATENT DOCUMENTS

| | | |
|---|---|---|
| DE | 10316159 A1 | 10/2004 |
| JP | 2006-038816 A | 2/2009 |
| WO | WO-87/06956 A1 | 11/1987 |
| WO | WO-95/26416 A1 | 10/1995 |
| WO | WO-01/57501 A1 | 8/2001 |

(Continued)

OTHER PUBLICATIONS

"International Application Serial No. PCT/CN2007/000020, International Search Report mailed Oct. 25, 2007", 6 pgs.

(Continued)

*Primary Examiner* — David Porta
*Assistant Examiner* — Marcus Taningco
(74) *Attorney, Agent, or Firm* — Schwegman, Lundberg & Woessner P.A.

(57) ABSTRACT

A microarray reader (100) comprises a light source (102), beam shaping elements (104) positioned near the light source (102), a moving stage (124) supporting one or more of the light source (102) and beam shaping elements (104), an optical substrate (112) supporting an immobilized microarray, a reaction chamber (116) in contact with the optical substrate (112) and encapsulating buffer solution, a heating/cooling component (118) in contact with the reaction chamber (116), a synchronization circuit, an optical filter (108) and an imaging sensor (106) positioned near the optical filter (108).

7 Claims, 4 Drawing Sheets

U.S. PATENT DOCUMENTS

| | | | |
|---|---|---|---|
| 2003/0124599 A1 | 7/2003 | Chen et al. | |
| 2003/0129770 A1 | 7/2003 | Fernandez | |
| 2003/0148391 A1 | 8/2003 | Salafsky | |
| 2003/0232427 A1* | 12/2003 | Montagu | 435/287.2 |
| 2003/0235518 A1 | 12/2003 | Shea et al. | |
| 2004/0009612 A1 | 1/2004 | Zhao et al. | |
| 2004/0125370 A1* | 7/2004 | Montagu | 356/244 |
| 2005/0014286 A1* | 1/2005 | Furuki et al. | 436/514 |
| 2005/0026209 A1 | 2/2005 | Vann | |
| 2005/0046848 A1* | 3/2005 | Cromwell et al. | 356/417 |
| 2005/0186565 A1* | 8/2005 | Malak | 435/5 |
| 2006/0088844 A1* | 4/2006 | Xu | 435/6 |
| 2008/0117425 A1* | 5/2008 | Kain | 356/455 |
| 2009/0088338 A1* | 4/2009 | Liu et al. | 506/9 |

FOREIGN PATENT DOCUMENTS

| | | |
|---|---|---|
| WO | WO-03/062791 A2 | 7/2003 |
| WO | WO-2005/118773 A2 | 12/2005 |
| WO | WO-2006/011346 A1 | 2/2006 |
| WO | WO-2006/135437 A2 | 12/2006 |

OTHER PUBLICATIONS

"International Application Serial No. PCT/CN2007/000020, Written Opinion mailed Oct. 2, 2007", 6 pgs.

Liu, X., et al., "A Fiber-Optic Evanescent Wave DNA Biosensor Based on Novel Molecular Beacons", *Analytical Chemistry*, 71(22), (Nov. 15, 1999), 5054-5059.

Peter, C., et al., "Optical DNA-sensor chip for real-time detection of hybridization events" *Fresenius Journal of Analytical Chemistry*, 371(2), (2001), 120-127.

"U.S. Appl. No. 10/972,033, Non Final Office Action mailed Mar. 11, 2008", 11 pgs.

"U.S. Appl. No. 10/972,033, Advisory Action mailed Dec. 17, 2007", 3 pgs.

"U.S. Appl. No. 10/972,033, Amendment and Response filed Dec. 6, 2007 to Final Ofice Action mailed Sep. 6, 2007", 6 pgs.

"U.S. Appl. No. 10/972,033, Final Office Action mailed Sep. 6, 2007", 10 pgs.

"U.S. Appl. No. 10/972,033, Final Office Action mailed Oct. 3, 2008", 18 pgs.

"U.S. Appl. No. 10/972,033, Final Office Action mailed Nov. 9, 2009", 21 pgs.

"U.S. Appl. No. 10/972,033, Non Final Office Action mailed Mar. 27, 2007", 12 pgs.

"U.S. Appl. No. 10/972,033, Non-Final Office Action mailed Apr. 2, 2009", 17 pgs.

"U.S. Appl. No. 10/972,033, Response filed Jan. 22, 2007 to Restriction Requirement mailed Dec. 20, 2006", 5 pgs.

"U.S. Appl. No. 10/972,033, Response filed Feb. 9, 2010 to Final Office Action mailed Nov. 9, 2009", 10 pgs.

"U.S. Appl. No. 10/972,033, Response filed Jun. 21, 2007 to Non Final Office Action mailed Mar. 27, 2007", 6 pgs.

"U.S. Appl. No. 10/972,033, Response filed Jun. 29, 2010 to Non Final Office Action mailed Mar. 31, 2010", 11 pgs.

"U.S. Appl. No. 10/972,033, Response filed Jul. 1, 2009 to Non Final Office Action mailed Apr. 2, 2009", 10 pgs.

"U.S. Appl. No. 10/972,033, Response filed Jun. 5, 2008 to Non Final Office Action mailed Mar. 11, 2008", 8 pgs.

"U.S. Appl. No. 10/972,033, Restriction Requirement mailed Dec. 20, 2006", 5 pgs.

"U.S. Appl. No. 10/972033, Response filed Jan. 5, 2009 to Final Office Action mailed Oct. 3, 2008", 9 pgs.

"U.S. Appl. No. 10/972,033, Non-Final Office Action mailed Mar. 31, 2010", 22 pgs.

"Chinese Application Serial No. 200580044154, First Office Action mailed on Apr. 30, 2010", (w/ English Translation), 12 pgs.

"Chinese Application Serial No. 200780049987.4, First Office Action mailed Apr. 26, 2010", (w/ English Translation), 16 pgs.

"International Application Serial No. PCT/US2005/037833, International Search Report mailed Jan. 22, 2007", 4 pgs.

"International Application Serial No. PCT/US2005/037833, Written Opinion mailed Jan. 22, 2007", 8 pgs.

Afanassiev, V., et al., "Preparation of DNA and protein micro arrays on glass slides coated with an agarose film", Nucleic Acids Research. 28(12), (2000), i-v.

Bustin, S. A., et al., "Quantification of mRNA using real-time reverse transcription PCR (RT-PCR): trends and problems", *Journal of Molecular Endocrinology*, 29. (2002), 23-39.

Soper, S. A., et al., "Nanoliter-scale sample preparation methods directly coupled to polymethylmethacrylate-based microchips and gel-filled capillaries for the analysis of oligonucleotides", Journal of Chromatography A, 853(1-2), (Aug. 20, 1999), 107-120.

Szuhai, K., et al., "A Novel Strategy for Human Papillomavirus Detection and Genotyping with SybrGreen and Molecular Beacon Polymerase Chain Reaction", American Journal of Pathology, 159(5), (2001), 1651-1660.

Tolley, S. E, et al., "Single-chain polymorphism analysis in long QT syndrome using planar waveguide fluorescent biosensors", Analytical Biochemistry, 315(2), (Apr. 15, 2003), 223-237.

"U.S. Appl. No. 10/972,033, Advisory Action mailed Jan. 5, 2011", 3 pgs.

"U.S. Appl. No. 10/972,033, Final Office Action mailed Oct. 28, 2010", 21 pgs.

"U.S. Appl. No. 10/972,033, Non Final Office Action mailed Mar. 1, 2011", 21 pgs.

"U.S. Appl. No. 10/972,033, Response filed Dec. 28, 2010 to Final Office Action mailed Oct. 28, 2010", 11 pgs.

"U.S. Appl. No. 12, 325,913, Response filed Jan. 26, 2011 to Restriction Requirement mailed Dec. 29, 2010", 6 pgs.

"U.S. Appl. No. 12/325,913, Restriction Requirement mailed Dec. 29, 2010", 6 pgs.

"Chinese Application Serial No. 200780049987.4, Office Action mailed Jan. 12, 2011", 3 pgs.

"Chinese Application Serial No. 200580044154, Response filed Nov. 2, 2010 to Office Action dated Apr. 30, 2010", (w/ English Translation of Claims), 11 pgs.

"Chinese Application Serial No. 200780049987.4, Response filed Feb. 17, 2011 to Office Action dated Jan. 12, 2011", (w/ English Translation of Claims), 4 pgs.

Afanassiev, V., et al., "Preparation of DNA and protein micro arrays on glass slides coated with an agarose film", Nucleic Acids Research, 28(12), (2000), e66 (i-v).

Peter, C., et al., "Optical DNA-sensor chip for real-time detection of hybridization events", Fresenius Journal of Analytical Chemistry, 371(2), Optical DNA-sensor chip for real-time detection of hybridization events, (2001), 120-127.

Szuhai, K., et al., "A Novel Strategy for Human Papillomavirus Detection and Genotyping with SybrGreen and Molecular Beacon Polymerase Chain Reaction", American Journal of Pathology, 159(5), (2001), 1651-1660.

"U.S. Appl. No. 10/972,033, Response filed May 18, 2011 to Non Final Office Action mailed Mar. 1, 2011", 12 pgs.

"U.S. Appl. No. 12/325,913, Non Final Office Action mailed Mar. 30, 2011", 22 pgs.

"U.S. Appl. No. 12/325,913, Response filed Jun. 30, 2011 to Non Final Office Action mailed Mar. 30, 2011", 10 pgs.

"China Application No. 200580044154—Office Action Received", 3 pgs.

"Chinese Application Serial No. 200780049987.4, Office Action issued May 11, 2011", (w/ English Translation), 7 pgs.

"U.S. Appl. No. 10/972,033, Final Office Action mailed Aug. 18, 2011", 22 pgs.

"U.S. Appl. No. 12/325,913, Final Office Action mailed Aug. 15, 2011", 28 pgs.

"Chinese Application No. 200580044154, Response filed Aug. 5, 2011 to Second Office Action mailed May 25, 2011", (w/ English Translation of Claims), 8 pgs.

"Chinese Application Serial No. 200780049987.4, Response filed Jul. 25, 2011 to Office Action mailed May. 11, 2011"(w/ English Translation of Claims), 5 pgs.

\* cited by examiner

US 8,124,944 B2

MICROARRAY READER BASED ON EVANESCENT WAVE DETECTION AND METHOD OF READING A MICROARRAY

RELATED APPLICATIONS

This application is a nationalization under 35 U.S.C. §371 of PCT/CN2007/000020, filed 17 Jan. 2007 and published as WO 2008/092291 A1 on 7 Aug. 2008, which application and publication is incorporated herein by reference in its entirety.

TECHNICAL FIELD

Embodiments of the present invention relate to a microarray reader based on evanescent wave detection. More specifically, embodiments of the present invention relate to a microarray reader for real-time PCR microarray based on evanescent wave detection.

BACKGROUND

Microarray readers conventionally used are based on florescent label, confocal microscopy and evanescent field. Examples include florescent scanning confocal microscopy and total internal reflection (TIR) fluorescent microscopy. These readers have a small field of view and require precise moving parts to scan the array, which leads to costly and slow reading. One approach includes exciting the whole probe array by expanding light source with uniform intensity distribution. However, lower sensitivity results due to the lower excitation.

Microarray readers with waveguide structures can produce high sensitivity and are free of moving parts. These readers are not suitable for disposable chip applications though, because of the high costs of waveguide fabrication and rigid alignment and coupling requirements. None of the existing microarray readers can meet the need of real-time PCR microarray detection due to the unique requirements in temperature control and sampling synchronization.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Embodiments of the present invention relate a microarray reader comprising: a light source, beam shaping elements positioned near the light source, a moving stage supporting one or more of the light source and beam shaping elements, an optical substrate supporting an immobilized microarray, a reaction chamber in contact with the optical substrate and encapsulating a buffer solution, a heating/cooling component in contact with the reaction chamber, a synchronization circuit, an optical filter and an imaging sensor positioned near the optical filter.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the present invention relate to a microarray reader for real-time PCR microarray analysis with evanescent wave detection. The microarray reader is low cost, reliable and can be utilized in a number of microarray configurations. The microarray reader also has convenient control, fast reading and high sensitivity. The microarray reader includes temperature control as well as a sampling synchronization circuit. The reader analyzes the signal by line scanning mode and utilizes intensity calibration and uniformity calibration. The optical substrate may be used not only to support the microarray, but also as the medium for total internal reflection. A reflective or absorptive coating may be partially applied to the substrate to decrease scattering noise and also serve as a position marker.

Figure 1:
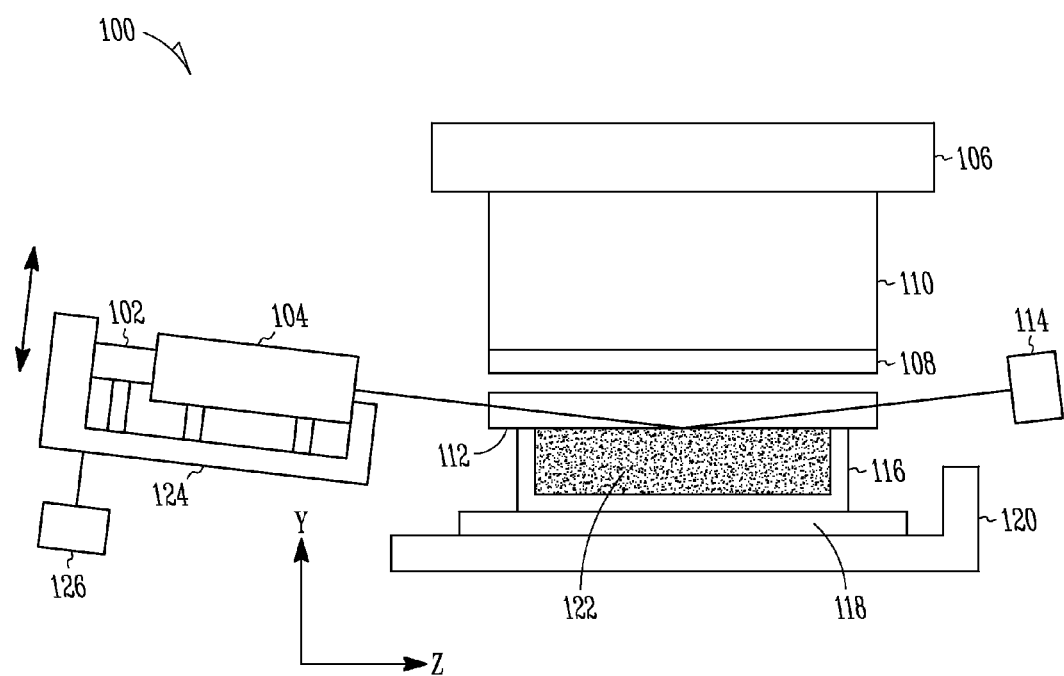
FIG. 1 illustrates a cross-sectional view of a microarray reader 100 based on evanescent wave detection, according to some embodiments.

Referring to FIG. 1, a cross-sectional view of a microarray reader 100 based on evanescent wave detection is shown, according to some embodiments. A linear translation stage 124 may support a line shape output light source 102, such as a laser. The wavelength of the light source 102 may be chosen to be in a range to activate the fluorescent tag. The light source 102 may be reshaped by cylindrical lenses 104 (beam shaping elements) before contacting substrate 112. Contacting may include entering the substrate 112, for example. The cylindrical lenses 104 may be diffraction optical elements or diffusing optical elements, for example.

The light source 102, cylindrical lenses 104 and linear translation stage 124 may make up a line scanning excitation system. The substrate 112 may be an optical substrate, such as glass or a polymer, for example. The substrate 112 may be very thin to decrease thermal capacity and meet the demands of rapid temperature control. The substrate 112 may be about 1 mm to about 3 mm thick, for example. The substrate 112 may be manufactured of a low autofluorescent material at the excitation wavelength.

Figure 3:
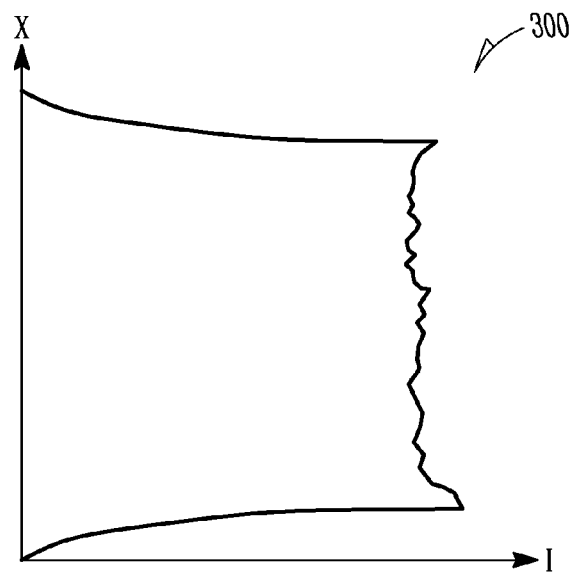
FIG. 3 illustrates a graphical view of an intensity profile of a line shape output light source, according to some embodiments.

The line scanning excitation system may sustain uniform intensity (as shown in FIG. 3). Uniform line scanning with uniformity calibration may be applied to overcome the lower speed for spot scanning, for example. To get flexible and convenient coupling, direct coupling may be applied, for example. Position variation of excitation may be adjusted by feedback control, for example. A synchronization circuit (126) may be utilized by the line scanning excitation system to synchronize sampling, for example.

The substrate 112 may contact a reaction chamber 116, encapsulating a buffer solution 122 and making up a real-time PCR microarray reaction system. The refractive index of the substrate 112 may be higher than the buffer solution 122, for example. The substrate may be glued to the reaction chamber 116, for example. The fluorescent tag may be imaged in an imaging sensor 106, such as a cooled CCD camera 106 by imaging lenses 110. An optical filter 108 between the substrate 112 and image lenses 110 may be utilized to block the exciting light and pass the fluorescence. In contact with the reaction chamber 116, a heating/cooling element 118 on a stage 120 may be utilized for heating, cooling or stabilization of the reaction system. The element 118 may be a TEC temperature control plate, for example. Variation of any light source intensity may be monitored by detector 114, such as a photo-electric detector.

Figure 2:
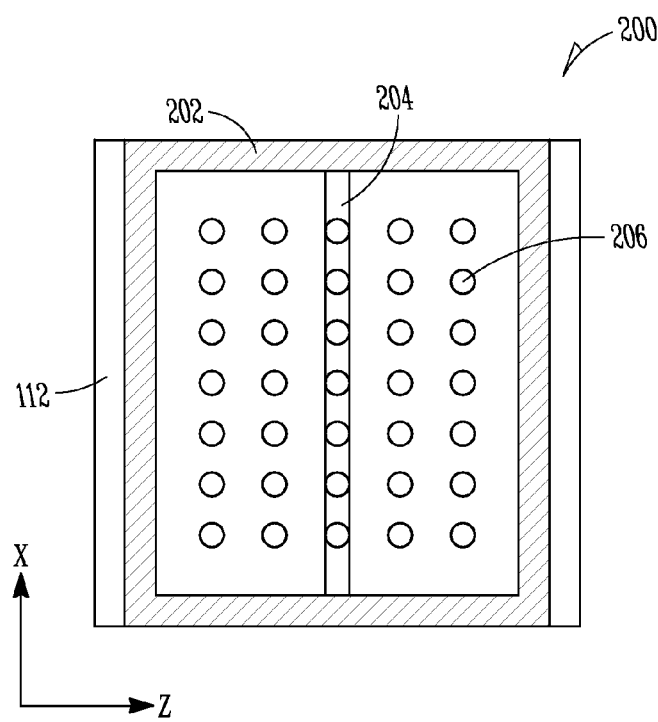
FIG. 2 illustrates a perspective view of an optical substrate 200, according to some embodiments.

Referring to FIG. 2, a perspective view of an optical substrate 200 is shown, according to some embodiments. To prevent any scattering caused by an adhesive, a multi-layer reflective or absorptive coating 202 may be coated on the adhesion area on the bottom side of the substrate 200. The coating 202 may also serve as a position marker, for example. Towards the bottom side of the substrate 200, total internal reflection may occur where probe array 206 may be immobilized on the surface. The optical substrate 200 may not only serve as the solid support for the microarray, but also as the optical dense media for the total internal reflection, for example. A column of array probe combined with florescent labeled target may be excited by line shape 204 evanescent field. To decrease the scattering at the optical substrate surface 200, facets of the substrate 112 may be fine polished. For example, four facets may be fine polished. For example, the left side surface, right side surface, upper side surface and bottom side surface may be polished. The surface quality of the optical substrate 200 may be better than 40-20 scratch-dig MIL-O-13830, for example.

Figure 4:
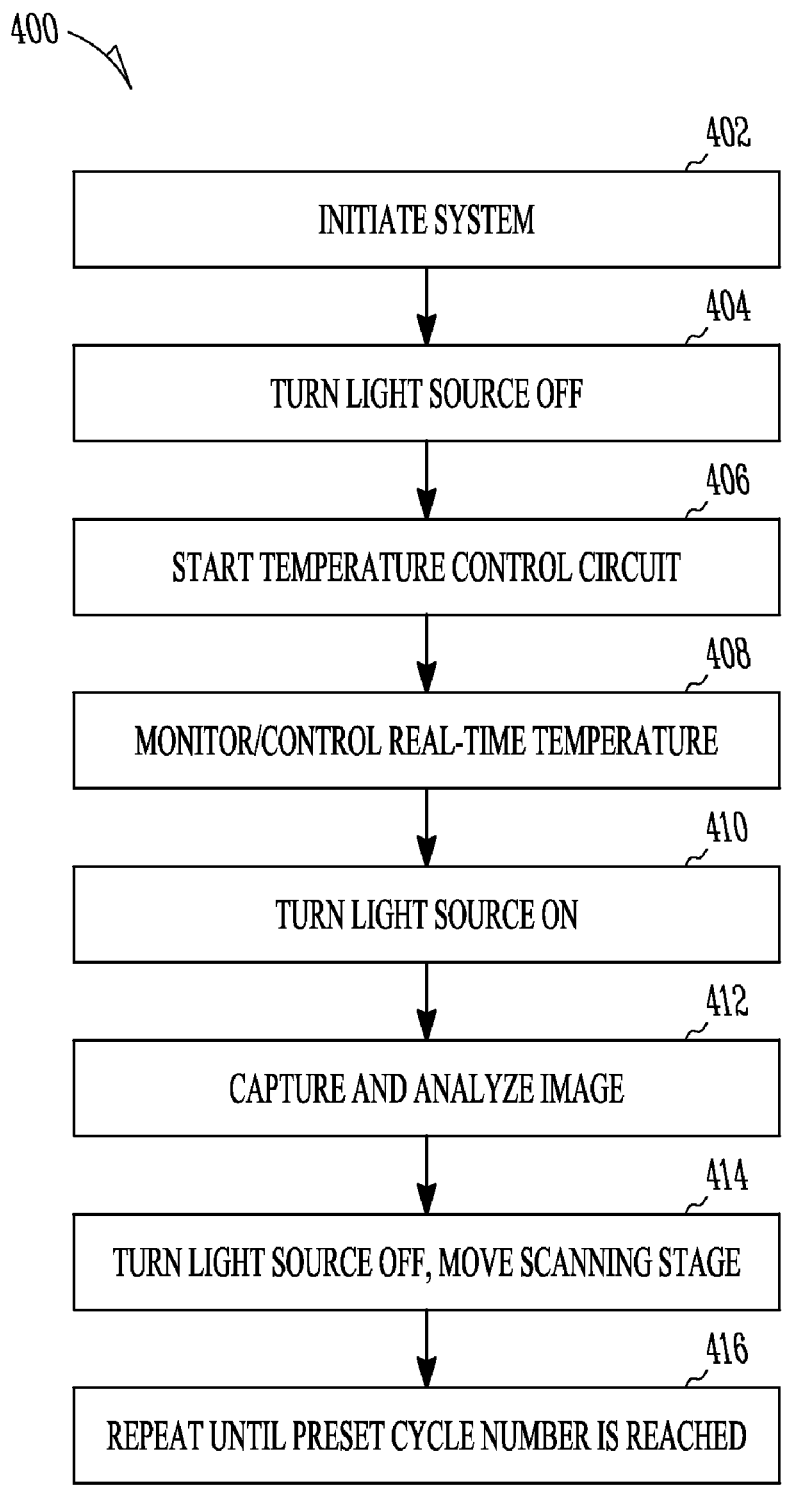
FIG. 4 illustrates a block flow diagram of a method of reading a microarray, according to some embodiments.

Referring to FIG. 4, a block flow diagram of a method 400 of reading a microarray is shown, according to some embodiments. The microarray reader system may be initiated 402, the light source may be turned off 404 before imaging capture and temperature control circuit initiated 406. The real-time temperature control may be monitored 408 during the entire reading process. The light source may be turned back on 410. Image capture and analysis 412 may be executed after the temperature reaches the preset sampling temperature. The light source may then be turned off and scanning station moved 414 to the next position. Steps 408 through 414 may be repeated until the preset cycle number has been reached 416.

System initiation 402 may include light source intensity calibration, line uniformity calibration, light source orientation, temperature parameter configuration, image setup or combinations thereof. Image analysis may be used for calibration, for example.

Figure 5:
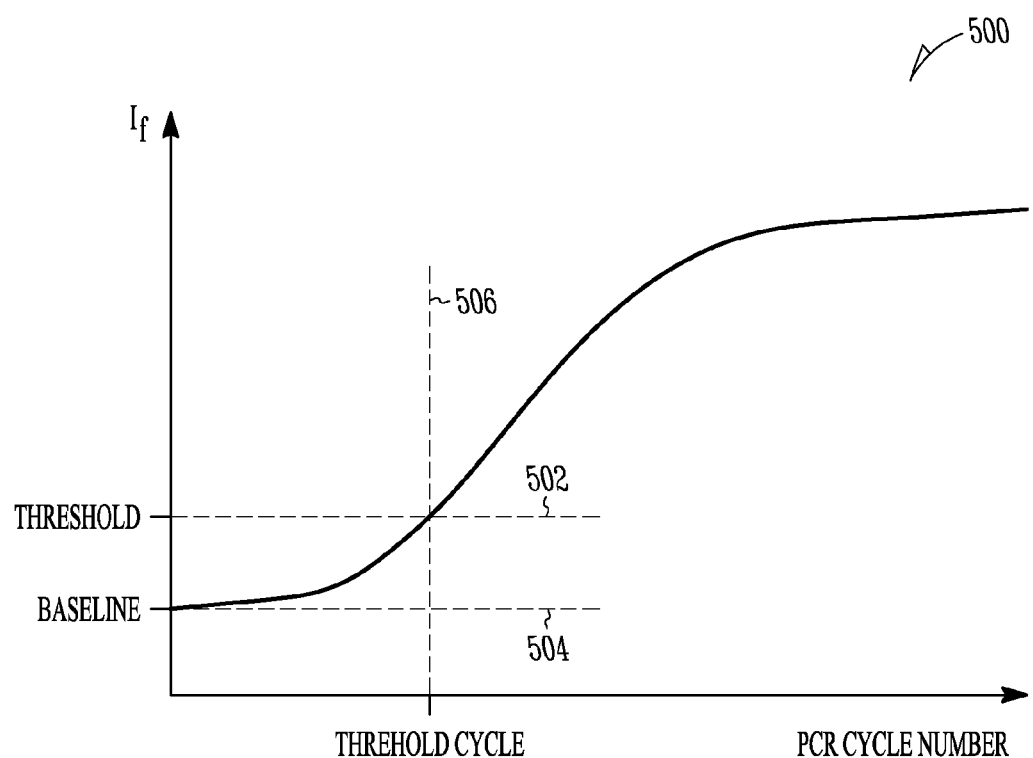
FIG. 5 illustrates a graphical view of an exemplary fluorescent labeled PCR signal curve, according to some embodiments.

Referring to FIG. 5, a graphical view of an exemplary fluorescent labeled PCR signal curve 500 is shown, according to some embodiments. A fluorescent labeled PCR signal curve is plotted versus the PCR cycle number. The background florescent baseline 504 marks the beginning of the PCR cycle. At the threshold cycle 506, florescent signal greatly increases versus time. The log of the initial target substance number is proportional to the threshold cycle 506. The number of target substance may be deduced from threshold cycle analysis.

The microarray of the embodiments of the present invention may be utilized with the microarray procedure of the following example, such as in copending U.S. patent application Ser. No. 10/972,033, filed Oct. 22, 2004, A PCR buffer contains fluorescently-tagged dNTPs, i.e., dNTPs having a fluorescent dye molecule attached to them, so that upon completion of each PCR cycle, the amplicons produced are fluorescently tagged. The amplicons of the target DNA are then localized, using probe strands of DNA known as oligoprobes. The oligoprobes have the complementary, nucleotide sequence as the target DNA. The oligopobes are tethered to a substrate surface in a known, two-dimensional pattern, with the substrate surface forming part of the reaction cell containing the PCR ingredients.

During the annealing and extension phases of the PCR process, the fluorescently-tagged, target amplicons hybridize to their corresponding oligoprobes. The hybridized, fluorescently tagged target amplicons are then illuminated with an evanescent wave of light of the appropriate wave-length to activate the fluorescent dye molecules of the tagged dNTPs. This evanescent wave decays exponentially in power after entering the reaction cell via the substrate surface to which the oligoprobes are tethered, with an effective penetration range of about 300 nm. This means that the evanescent wave penetrates far enough into the reaction cell to activate the fluorescently tagged amplicons hybridized to those oligopobes, but that it does not activate the fluorescently tagged dNTPS in solution in the main body of the reaction cell. By monitoring the strength of the fluorescence at various locations on the substrate surface, the current abundance of amplicons of the corresponding, target DNA can be determined. This may be done in real time as the PCR reaction progresses, and the results used to obtain a quantitative measure of the abundance of a specific target in the original sample, in a manner analogous to the real time PCR calculation.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A microarray-reader, comprising:
    a light source;
    beam shaping elements, positioned near the light source;
    a moving stage, supporting one or more of the light source and beam shaping elements;
    an optical substrate, supporting an immobilized microarray;
    a reaction chamber, in contact with the optical substrate and encapsulating a buffer solution;

a heating/cooling component, in contact with the reaction chamber;

a synchronization circuit;

an optical filter; and an imaging sensor, positioned near the optical filter;

wherein the substrate is at least partially contacted with a multilayer reflective or absorptive coating that acts as a position marker.

2. The microarray reader of claim 1, wherein the buffer solution supports a PCR reaction.

3. The microarray reader of claim 1, wherein the substrate is an optical density media.

4. The microarray reader of claim 1, wherein the substrate is about 1 mm to about 3 mm in thickness.

5. The microarray reader of claim 1, wherein the imaging sensor comprises a CCD camera.

6. The microarray-reader of claim 1, wherein light from the beam shaping elements strikes the optical substrate directly, and the light source, the beam shaping elements, and the moving stage make up a line scanning excitation system to apply line scanning.

7. The microarray reader of claim 1, wherein the line scanning is uniform.

* * * * *